(12) United States Patent
Schlueter

(10) Patent No.: US 7,909,458 B2
(45) Date of Patent: Mar. 22, 2011

(54) UV-ABSORBERS FOR OPHTHALMIC LENS MATERIALS

(75) Inventor: Douglas C. Schlueter, Azle, TX (US)

(73) Assignee: Alcon, Inc., Hunenberg (CH)

( * ) Notice: Subject to any disclaimer, the term of this patent is extended or adjusted under 35 U.S.C. 154(b) by 415 days.

(21) Appl. No.: 12/111,321

(22) Filed: Apr. 29, 2008

(65) Prior Publication Data

US 2008/0266519 A1   Oct. 30, 2008

Related U.S. Application Data

(60) Provisional application No. 60/914,923, filed on Apr. 30, 2007.

(51) Int. Cl.
  *G02C 7/04* (2006.01)
(52) U.S. Cl. .................. 351/160 R; 548/255; 623/6.56
(58) Field of Classification Search ............. 351/160 R; 548/255; 623/6.56
See application file for complete search history.

(56) References Cited

U.S. PATENT DOCUMENTS

| | | | |
|---|---|---|---|
| 3,880,875 A | 4/1975 | Strobel et al. ................ 260/308 |
| 5,290,892 A | 3/1994 | Namdaran et al. ............ 526/259 |
| 5,331,073 A | 7/1994 | Weinschenk, III et al. ... 526/264 |
| 5,470,932 A | 11/1995 | Jinkerson ..................... 526/312 |
| 5,693,095 A | 12/1997 | Freeman et al. ................. 623/6 |
| 6,166,218 A | 12/2000 | Ravichandran et al. |
| 6,528,602 B1 | 3/2003 | Freeman et al. .............. 526/259 |
| 6,806,337 B2 | 10/2004 | Schlueter et al. ......... 526/318.43 |
| 6,846,897 B2 | 1/2005 | Salamone et al. ............... 528/43 |
| 6,852,793 B2 | 2/2005 | Salamone et al. ............ 524/560 |
| 6,872,793 B1 | 3/2005 | Schlueter ..................... 526/326 |
| 7,037,954 B2 | 5/2006 | Baba et al. ....................... 522/99 |
| 7,067,602 B2 | 6/2006 | Benz et al. .................. 526/329.6 |
| 7,101,949 B2 | 9/2006 | Salamone et al. ............... 528/43 |
| 7,119,210 B2 | 10/2006 | Schlueter ..................... 548/260 |
| 7,326,423 B2 | 2/2008 | Pearson et al. ................ 424/427 |
| 7,396,942 B2 | 7/2008 | Schlueter ....................... 549/27 |
| 7,728,051 B2 * | 6/2010 | Weinschenk et al. ......... 523/106 |
| 2002/0042653 A1 | 4/2002 | Copeland et al. ............... 623/6.6 |
| 2005/0222427 A1 | 10/2005 | Sharpless et al. .......... 548/262.2 |
| 2006/0252844 A1 | 11/2006 | Mentak ......................... 523/106 |
| 2006/0252850 A1 | 11/2006 | Jani et al. ...................... 523/160 |
| 2007/0092830 A1 | 4/2007 | Lai et al. .................... 530/270.1 |
| 2007/0092831 A1 | 4/2007 | Lai et al. |
| 2008/0090937 A1 | 4/2008 | Jinkerson et al. ............. 523/108 |
| 2008/0242818 A1 | 10/2008 | Benz et al. |

FOREIGN PATENT DOCUMENTS

| | | |
|---|---|---|
| CN | 1727338 | 2/2006 |
| EP | 0 989 124 A1 | 3/2000 |
| EP | 1 033 590 B1 | 5/2008 |
| FR | 2 099 154 | 3/1972 |
| JP | 2005053058 | 3/2005 |
| JP | 2009013148 | 1/2009 |
| WO | WO 2006/121876 | 11/2006 |
| WO | WO2008109624 A2 | 9/2008 |

OTHER PUBLICATIONS

Pagliai et al. (J. Med. Chem. 2006, 49(2); 467-470).*
Vogt and Sumerlin (Macromolecules, 2006, 39; 5286-5292).*
Hawker et al., "The Convergence of Synthetic Organic and Polymer Chemistries," *Science*, vol. 309, pp. 1200-1205 (2005).
Kolb et al., "Click Chemistry: Diverse Chemical Function from a Few Good Reactions," *Angew. Chem. Int. Ed.*, vol. 40, pp. 2004-2021 (2001).
Ladmiral et al., "Synthesis of Neoglycopolymers by a Combination of "Click Chemistry" and Living Radical Polymerization," *J. American Chemical Societyl*, vol. 128, pp. 4823-4830 (2006).
Rostovtsev et al., "A Stepwise Huisgen Cycloaddition Process: Copper(I)-Catalyzed Regioselective "Ligation" of Azides and Terminal Alkynes," *Angew Chem. Int. Ed*, vol. 41(14), pp. 2596-2599 (2002).
Thibault et al., "Combination of LFRP and Click Chemistry for Orthogonal Modification of Well-defined Terpolymers," *Polymer Preprints*, vol. 46(1), p. 10 (2005).
Vogt et al., "An Efficient Route to Macromonomers via ATRP and Click Chemistry," *Macromolecules*, vol. 39, pp. 5286-5292 (2006).

* cited by examiner

*Primary Examiner* — Yong Chu
*Assistant Examiner* — Valerie Rodriguez-Garcia
(74) *Attorney, Agent, or Firm* — Patrick M. Ryan

(57) ABSTRACT

1,4-disubstituted-1,2,3-triazole UV absorbing monomers are disclosed. The UV absorbers are particularly suitable for use in intraocular lens materials.

16 Claims, No Drawings

UV-ABSORBERS FOR OPHTHALMIC LENS MATERIALS

This application claims priority to U.S. Provisional Application, U.S. Ser. No. 60/914,923 filed Apr. 30, 2007.

FIELD OF THE INVENTION

This invention is directed to ultraviolet light absorbers. In particular, this invention relates to 1,4-disubstituted-1,2,3-triazole UV light absorbing monomers.

BACKGROUND OF THE INVENTION

Many UV light absorbers are known as ingredients for polymeric materials used to make ophthalmic lenses. UV absorbers are preferably covalently bound to the polymeric network of the lens material instead of simply physically entrapped in the material to prevent the absorber from migrating, phase separating or leaching out of the lens material. Such stability is particularly important for implantable ophthalmic lenses where the leaching of the UV absorber may present both toxicological issues and lead to the loss of UV blocking activity in the implant.

Numerous copolymerizable benzatriazole, benzophenone and triazine UV absorbers are known. Many of these UV absorbers contain conventional olefinic polymerizable groups, such as methacrylate, acrylate, methacrylamide, acrylamide or styrene groups. Copolymerization with other ingredients in the lens materials, typically with a radical initiator, incorporates the UV absorbers into the resulting polymer chain. Incorporation of additional functional groups, on a UV absorber may influence one or more of the UV absorber's UV absorbing properties, solubility or reactivity. If the UV absorber does not have sufficient solubility in the remainder of the ophthalmic lens material ingredients or polymeric lens material, the UV absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

SUMMARY OF THE INVENTION

The present invention provides 1,4-disubstituted-1,2,3-triazole UV light absorbing monomers. These UV absorbers are suitable for use in ophthalmic lenses, including contact lenses. They are particularly useful in implantable lenses, such as intraocular lenses (IOLs).

DETAILED DESCRIPTION OF THE INVENTION

Unless indicated otherwise, all ingredient amounts expressed in percentage terms are presented as % w/w.

The UV absorbers of the present invention are represented by the formula

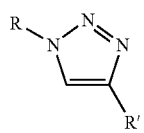

where

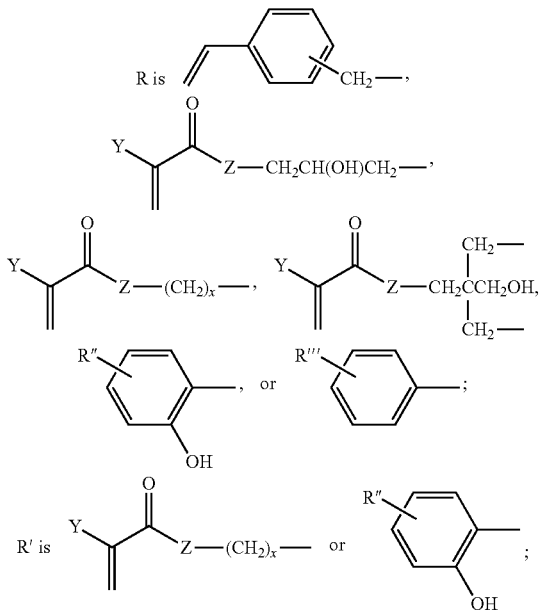

x is 1-12;
Y is H, $CH_3$, $CH_2OH$, or $CH_3CH_2$;
Z is O, NH, $N(CH_3)$, or $N(CH_2CH_3)$;
Z' is O, NH, $N(CH_3)$, or $N(CH_2CH_3)$;
R" is H, F, Cl, Br, I, $O(CH_2)_xH$, $NH_2$, $NH(CH_3)$, $N(CH_3)_2$, $CH_3$, $CH_2CH_3$, $CH(CH_3)_2$, $C(CH_3)_3$, $C_6H_5$, or $OC_6H_5$; and
R''' is $CH_2$=CH—, $CH_2$=$(CH_3)$—, or

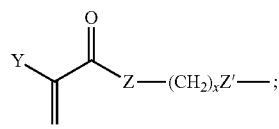

provided that one, but not both, of R and R' is

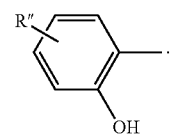

Preferred UV absorbers of the present invention are those of formulas [1]-[3]:

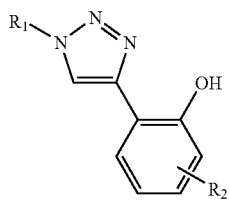

[1]

where in formula [1]

$R_1$ is

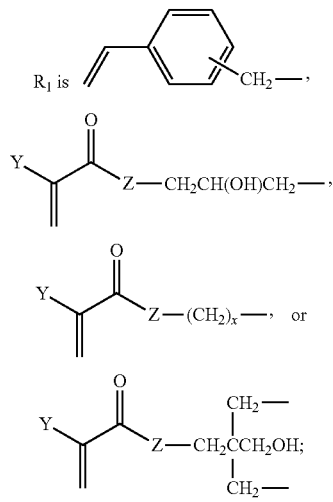

x is 1-12;
Y is H, $CH_3$, or $CH_3CH_2$;
Z is O, NH, $N(CH_3)$, or $N(CH_2CH_3)$; and
$R_2$ is H, F, Cl, Br, I, $O(CH_2)_xH$, $NH_2$, $NH(CH_3)$, $N(CH_3)_2$, $CH_3$, $CH_2CH_3$, $CH(CH_3)_2$, $C(CH_3)_3$, $C_6H_5$, or $OC_6H_5$;

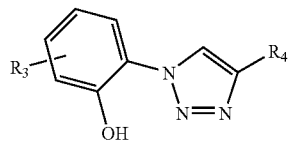

where in formula [2]
$R_3$ is H, F, Cl, Br, I, $O(CH_2)_xH$, $NH_2$, $NH(CH_3)$, $N(CH_3)_2$, $CH_3$, $CH_2CH_3$, $CH(CH_3)_2$, $C(CH_3)_3$, $C_6H_5$, or $OC_6H_5$;
$R_4$ is

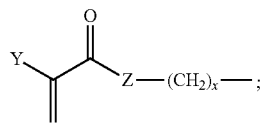

x is 1-12;
Y is H, $CH_3$, or $CH_3CH_2$; and
Z is O, NH, $N(CH_3)$, or $N(CH_2CH_3)$; and

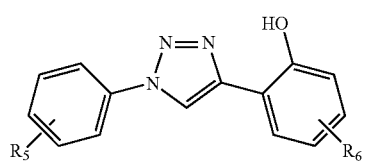

where in formula [3]
$R_5$ is $CH_2$=CH—, $CH_2$=C($CH_3$)—, or

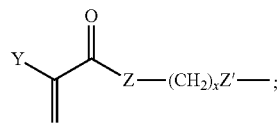

$R_6$ is H, F, Cl, Br, I, $O(CH_2)_xH$, $NH_2$, $NH(CH_3)$, $N(CH_3)_2$, $CH_3$, $CH_2CH_3$, $CH(CH_3)_2$, $C(CH_3)_3$, $C_6H_5$, or $OC_6H_5$;
x is 0-12;
Y is H, $CH_3$, or $CH_3CH_2$;
Z is O, NH, $N(CH_3)$, $N(CH_2CH_3)$, or nothing; and
Z' is O, NH, $N(CH_3)$, $N(CH_2CH_3)$, or nothing;
provided that if x is 0, then Z≠nothing and Z'=nothing.

The synthesis of the UV absorbers of the present invention is described below. In Scheme 1, an aliphatic azide is coupled with an o-alkynylphenol in a single step to produce the target phenyl substituted 1,2,3-triazole where the placement of the phenol group next to the triazole is considered for desired UV absorbance characteristics. For example, azidoethyl methacrylate with 2-ethynyl-phenol will produce a 1,2,3-triazole functional polymerizable UV absorber in a single step. Additional hydroxyl functionality is envisioned through use of propanediol or glycerol based aliphatic azides.

Scheme 1. Synthesis of 1,2,3-triazole functional polymerizable UV absorbers from aliphatic azide and aromatic alkyne.

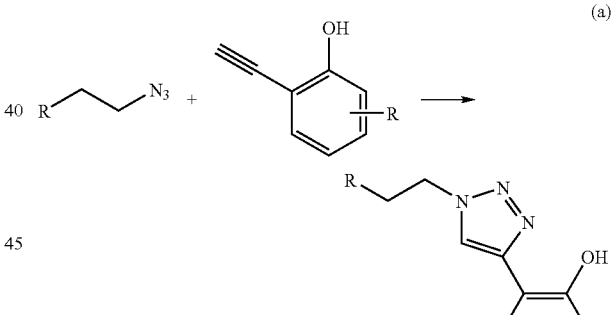

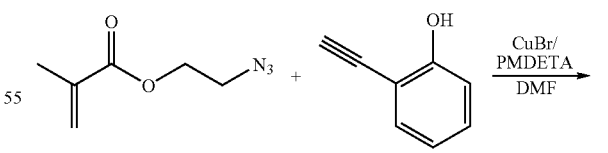

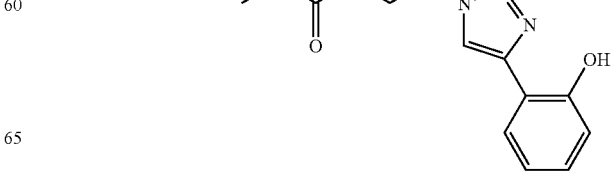

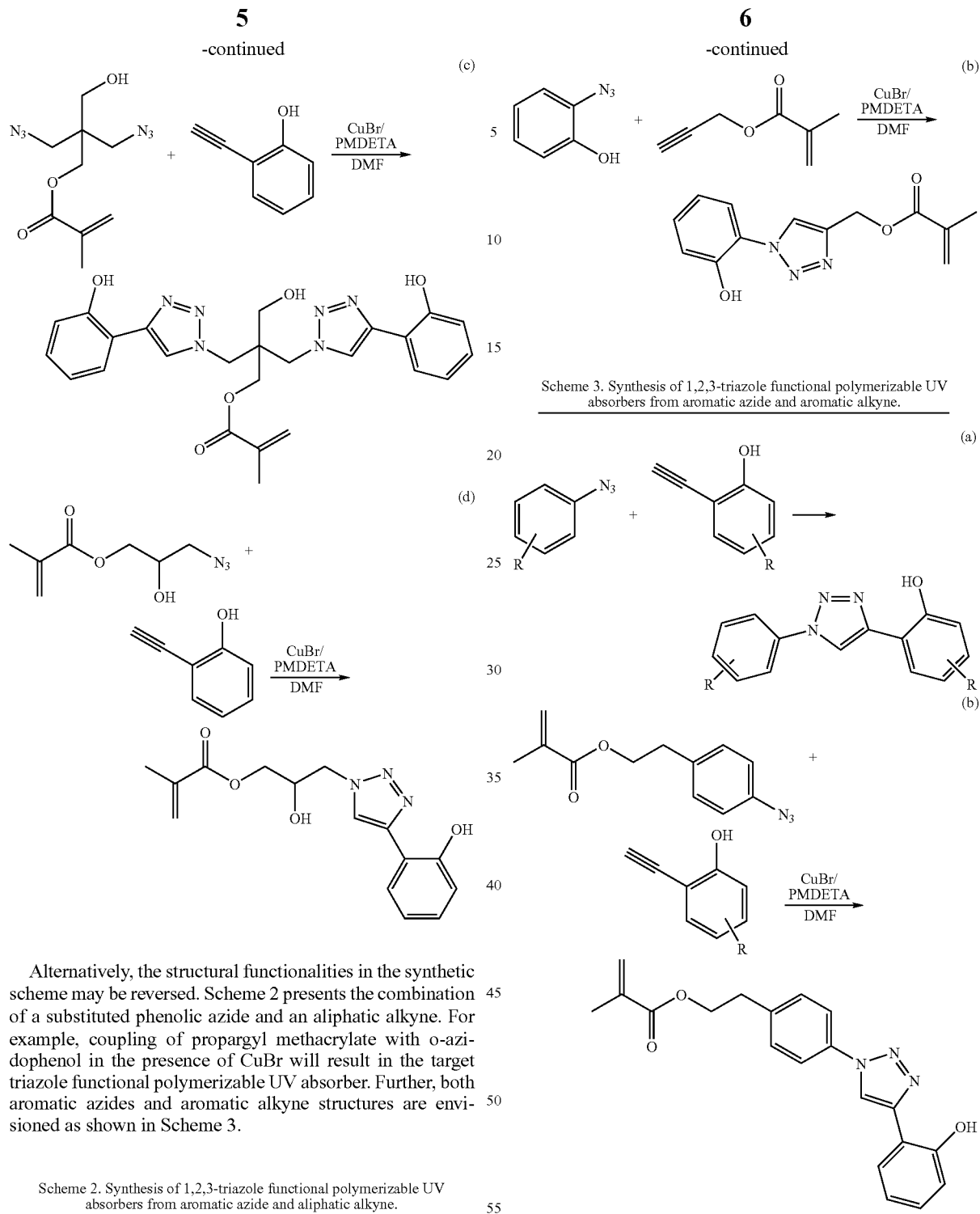

Scheme 3. Synthesis of 1,2,3-triazole functional polymerizable UV absorbers from aromatic azide and aromatic alkyne.

Alternatively, the structural functionalities in the synthetic scheme may be reversed. Scheme 2 presents the combination of a substituted phenolic azide and an aliphatic alkyne. For example, coupling of propargyl methacrylate with o-azidophenol in the presence of CuBr will result in the target triazole functional polymerizable UV absorber. Further, both aromatic azides and aromatic alkyne structures are envisioned as shown in Scheme 3.

Scheme 2. Synthesis of 1,2,3-triazole functional polymerizable UV absorbers from aromatic azide and aliphatic alkyne.

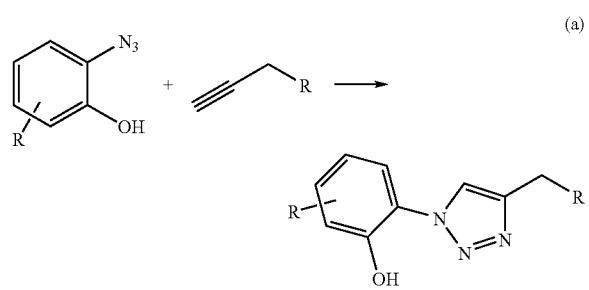

The UV absorbers of the present invention are particularly suitable for use in IOLs. IOL materials will generally contain from 0.1 to 5% (w/w) of a UV absorber of the present invention. Preferably, IOL materials will contain from 0.5 to 3% (w/w) of a UV absorber of the present invention. Such device materials are prepared by copolymerizing the UV absorbers of the present invention with other ingredients, such as device-forming materials, cross-linking agents, and blue-light blocking chromophores.

Many device-forming monomers are known in the art and include both acrylic and silicone-containing monomers among others. See, for example, U.S. Pat. Nos. 7,101,949; 7,067,602; 7,037,954; 6,872,793 6,852,793; 6,846,897; 6,806,337; 6,528,602; and 5,693,095. In the case of IOLs, any known IOL device material is suitable for use in the compositions of the present invention. Preferably, the ophthalmic device materials comprise an acrylic or methacrylic device-forming monomer. More preferably, the device-forming monomers comprise a monomer of formula [IV]:

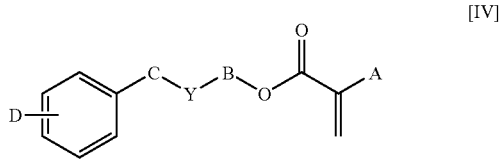

where in formula [IV]:
A is H, $CH_3$, $CH_2CH_3$, or $CH_2OH$;
B is $(CH_2)_m$ or $[O(CH_2)_2]_z$;
C is $(CH_2)_w$;
m is 2-6;
z is 1-10;
Y is nothing, O, S, or NR', provided that if Y is O, S, or NR', then B is $(CH_2)_m$;
R' is H, $CH_3$, $C_nH_{2n'+1}$ (n'=1-10), iso-$OC_3H_7$, $C_6H_5$, or $CH_2C_6H_5$;
w is 0-6, provided that m+w≦8; and
D is H, $C_1$-$C_4$ alkyl, $C_1$-$C_4$ alkoxy, $C_6H_5$, $CH_2C_6H_5$ or halogen.

Preferred monomers of formula [IV] are those wherein A is H or $CH_3$, B is $(CH_2)_m$, m is 2-5, Y is nothing or O, w is 0-1, and D is H. Most preferred are 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

Monomers of formula [IV] are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

Device materials generally comprise a total of at least about 75%, preferably at least about 80%, of device-forming monomers.

In addition to a UV absorber of the present invention and a device-forming monomer, the device materials of the present invention generally comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C$(=O)O—$(CH_2CH_2O)_p$—$C$(=O)$C(CH_3)$=$CH_2$ where p =1-50; and $CH_2$=$C(CH_3)C$(=O)O$(CH_2)_tO$—$C$(=O)$C(CH_3)$=$CH_2$ where t=3-20; and their corresponding acrylates. A preferred cross-linking monomer is $CH_2$=$C(CH_3)C$(=O)O—$(CH_2CH_2O)_p$—$C$(=O)$C(CH_3)$=$CH_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 0.1-17% (w/w).

Suitable polymerization initiators for device materials containing a UV absorber of the present invention include thermal initiators and photoinitiators. Preferred thermal initiators include peroxy free-radical initiators, such as t-butyl (peroxy-2-ethyl)hexanoate and di-(tert-butylcyclohexyl) peroxydicarbonate (commercially available as Perkadox® 16 from Akzo Chemicals Inc., Chicago, Ill.). Initiators are typically present in an amount of about 5% (w/w) or less. Because free-radical initiators do not become chemically a part of the polymers formed, the total amount of initiator is customarily not included when determining the amounts of other ingredients.

The device materials containing a UV absorber of the present invention preferably also contain a reactive colorant. Suitable reactive blue-light absorbing compounds include those described in U.S. Pat. No. 5,470,932. Blue-light absorbers are typically present in an amount from about 0.01-0.5% (weight).

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use in other ophthalmic devices, such as contact lenses, keratoprostheses, and corneal inlays or rings.

The invention will be further illustrated by the following examples, which are intended to be illustrative, but not limiting.

EXAMPLE 1

Synthesis of 1,2,3-triazole functional polymerizable UV absorber [UV-1]

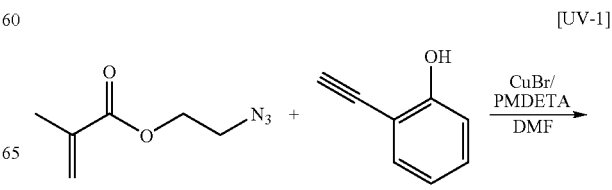

-continued

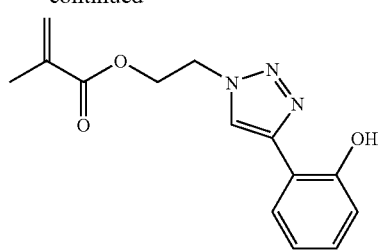

A 100 ml round bottom flask containing a PTFE coated stir bar is charged with 3.10 g of azido ethyl methacrylate (20 mmol), 2.36 g of o-hydroxyphenyl acetylene (20 mmol) and 50 mL of tetrahydrofuran. Copper turnings (1 g) were weighed and added. The flask was closed with a glass stopper and the reaction was stirred 48 h at ambient temperature. The copper was removed and the solvent was evaporated to yield product UV-1.

EXAMPLE 2

Synthesis of 1,2,3-triazole functional polymerizable UV absorber [UV-2]

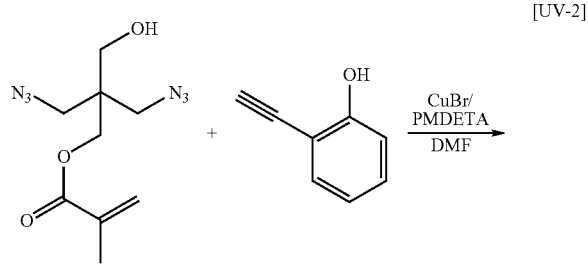

[UV-2]

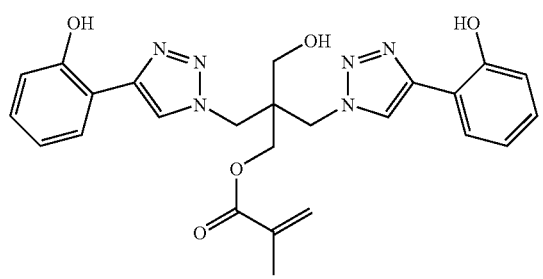

A 100 ml round bottom flask containing a PTFE coated stir bar is charged with 5.09 g of 3-azido-2-azidomethyl-2-hydroxymethyl-propyl methacrylate (20 mmol), 2.36 g of o-hydroxyphenyl acetylene (20 mmol) and 50 mL of tetrahydrofuran. Copper turnings (1 g) are added and the solution is stirred for 48 h at ambient temperature. The copper was removed and the solvent was evaporated to yield product UV-2.

EXAMPLE 3

Synthesis of 1,2,3-triazole functional polymerizable UV absorber [UV-3]

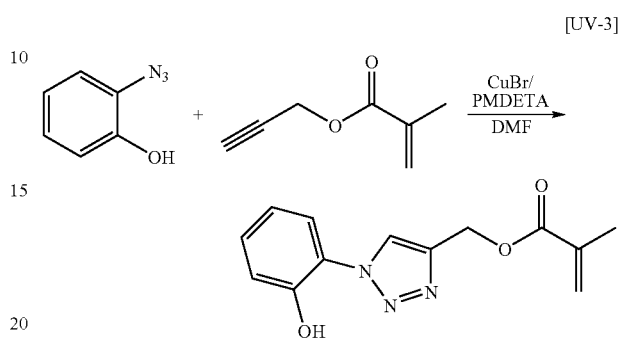

[UV-3]

A 100 ml round bottom flask containing a PTFE coated stir bar is flushed with $N_2$ and charged with 2.48 g of propargyl methacrylate (20 mmol), 2.70 g of 2-azidophenol (20 mmol), 50 mL of N,N-dimethylformamide, 3.54 g of N,N,N'N",N"-pentamethyldiethylenetriamine, and 2.87 g of CuBr. The solution is stirred for 24 h at ambient temperature under a $N_2$ blanket. The reaction mixture is then exposed to air and purified by passing through a chromatographic alumina column. The eluent is collected and the solvent is evaporated to yield product UV-3.

EXAMPLES 4-6

Copolymerization of 1,2,3-triazole functional polymerizable UV absorber

A vial is charged with ingredients as listed in Table 1 except for the initiator. The solution is mixed thoroughly and degassed by bubbling with $N_2$. The initiator is added and the solution is again mixed thoroughly. The solution is filtered through a 0.2 micron PTFE filter and transferred to polypropylene molds. The molds are heated in a mechanical convection oven at 70° C. for 1 hr, then 110° C. for 2 hrs. The resulting copolymer samples are removed from the polypropylene molds and extracted in refluxing acetone for at least 3 hr, then rinsed with fresh acetone and allowed to air dry. The extracted polymer is dried under vacuum at 70° C. for at least 3 hr.

TABLE 1

Representative Copolymer Formulations

| Ingredient | Amount (% w/w) | | |
|---|---|---|---|
| | 4 | 5 | 6 |
| PEA | 64.9 | 85.0 | 0.0 |
| PEMA | 30.0 | 0.0 | 0.0 |
| PBMA | 0.0 | 0.0 | 82.2 |
| HEMA | 0.0 | 15.0 | 0.0 |
| PEG(1000)DMA | 0.0 | 0.0 | 15.0 |
| EGDMA | 0.0 | 0.0 | 1.0 |
| BDDA | 3.2 | 3.2 | 0.0 |

TABLE 1-continued

Representative Copolymer Formulations

| Ingredient | Amount (% w/w) | | |
| --- | --- | --- | --- |
| | 4 | 5 | 6 |
| UV absorber [UV-1] | 1.8 | 1.8 | 1.8 |
| N-2-[3-(2'-methylphenylazo)-4-hydroxyphenyl]ethyl methacrylamide | 0.1 | 0.0 | 0.0 |
| Perkadox ® 16S | 1.0 | 1.0 | 1.0 |

PEA = 2-phenylethyl acrylate
PEMA = 2-phenylethyl methacrylate
PBMA = 4-phenylbutyl methacrylate
HEMA = 2-hydroxyethyl methacrylate
PEG(1000)DMA = polyethylene glycol (1000) dimethacrylate
EGDMA = ethylene glycol dimethacrylate
BDDA = 1,4-butanediol diacrylate This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

I claim:

1. A 1,4-disubstituted-1,2,3-triazole compound of the formula

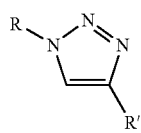

where

R is 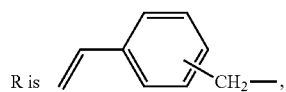,

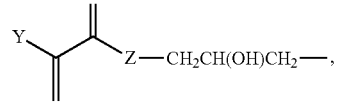,

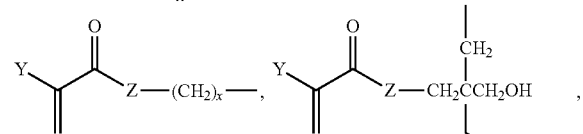,

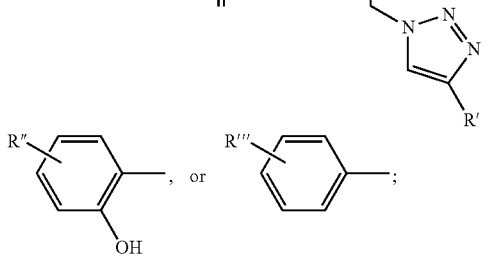

R' is 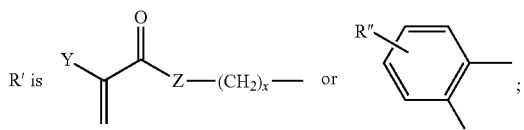

x is 1-12;
Y is H, $CH_3$, $CH_2OH$, or $CH_3CH_2$;
Z is O, NH, $N(CH_3)$, or $N(CH_2CH_3)$;
Z' is O, NH, $N(CH_3)$, or $N(CH_2CH_3)$;
R'' is H, F, Cl, Br, I, $O(CH_2)_xH$, $NH_2$, $NH(CH_3)$, $N(CH_3)_2$, $CH_3$, $CH_2CH_3$, $CH(CH_3)_2$, $C(CH_3)_3$, $C_6H_5$, or $OC_6H_5$; and
R''' is $CH_2{=}CH{-}$, $CH_2{=}C(CH_3){-}$, or

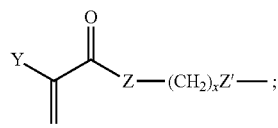

provided that one, but not both, of R and R' is

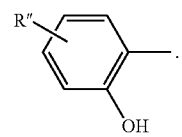

2. The 1,4-disubstituted-1,2,3-triazole compound of claim 1 wherein the compound has the formula

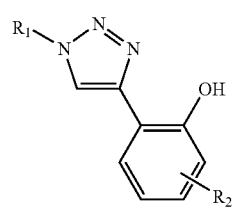

[1]

where in formula [1]

$R_1$ is 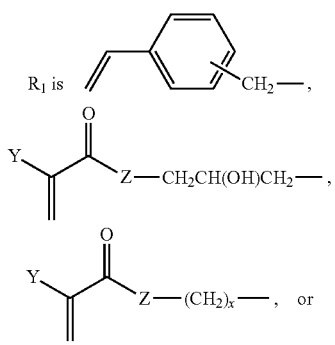

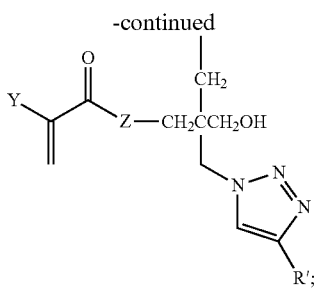

x is 1-12;
Y is H, CH$_3$, or CH$_3$CH$_2$;
Z is O, NH, N(CH$_3$), or N(CH$_2$CH$_3$); and
R$_2$ is H, F, Cl, Br, I, O(CH$_2$)$_x$H, NH$_2$, NH(CH$_3$), N(CH$_3$)$_2$, CH$_3$, CH$_2$CH$_3$, CH(CH$_3$)$_2$, C(CH$_3$)$_3$, C$_6$H$_5$, or OC$_6$H$_5$.

3. The 1,4-disubstituted-1,2,3-triazole compound of claim 1 wherein the compound has the formula

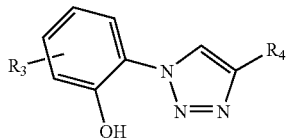

[2]

where in formula [2]
R$_3$ is H, F, Cl, Br, I, O(CH$_2$)$_x$H, NH$_2$, NH(CH$_3$), N(CH$_3$)$_2$, CH$_3$, CH$_2$CH$_3$, CH(CH$_3$)$_2$, C(CH$_3$)$_3$, C$_6$H$_5$, or OC$_6$H$_5$;
R$_4$ is

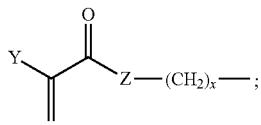

x is 1-12;
Y is H, CH$_3$, or CH$_3$CH$_2$; and
Z is O, NH, N(CH$_3$), or N(CH$_2$CH$_3$).

4. An ophthalmic device material comprising the 1,4-disubstituted-1,2,3-triazole compound of claim 1 and a device-forming monomer selected from the group consisting of acrylic monomers and silicone-containing monomers.

5. The ophthalmic device material of claim 4 wherein the ophthalmic device material comprises from 0.1 to 5% (w/w) of the 1,4-disubstituted-1,2,3-triazole compound.

6. The ophthalmic device material of claim 5 wherein the ophthalmic device material comprises from 0.5 to 3% (w/w) of the 1,4-disubstituted-1,2,3-triazole compound.

7. The ophthalmic device material of claim 4 wherein the ophthalmic device material comprises a device-forming monomer of formula [IV]:

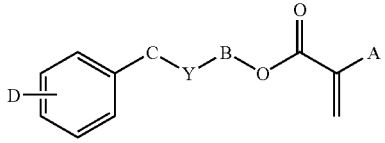

[IV]

where in formula [IV]:
A is H, CH$_3$, CH$_2$CH$_3$, or CH$_2$OH;
B is (CH$_2$)$_m$ or [O(CH$_2$)$_2$]$_z$;
C is (CH$_2$)$_w$;
m is 2-6;
z is 1-10;
Y is nothing, O, S, or NR', provided that if Y is O, S, or NR', then B is (CH$_2$)$_m$;
R' is H, CH$_3$, C$_{n'H2n'+1}$ (n'=1-10), iso-OC$_3$H$_7$, C$_6$H$_5$, or CH$_2$C$_6$H$_5$;
w is 0-6, provided that m+w≦8; and
D is H, C$_1$-C$_4$ alkyl, C$_1$-C$_4$ alkoxy, C$_6$H$_5$, CH$_2$C$_6$H$_5$ or halogen.

8. The ophthalmic device material of claim 7 wherein in formula [IV]:
A is H or CH$_3$;
B is (CH$_2$)$_m$;
m is 2-5;
Y is nothing or O;
w is 0-1; and
D is H.

9. The ophthalmic device material of claim 8 wherein the ophthalmic device material comprises a monomer selected from the group consisting of: 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

10. The ophthalmic device material of claim 4 wherein the ophthalmic device material comprises a cross-linking agent.

11. The ophthalmic device material of claim 4 wherein the ophthalmic device material comprises a reactive blue-light absorbing compound.

12. An intraocular lens comprising the 1,4-disubstituted-1,2,3-triazole compound of claim 1.

13. An intraocular lens comprising the 1,4-disubstituted-1,2,3-triazole compound of claim 2.

14. An intraocular lens comprising the 1,4-disubstituted-1,2,3-triazole compound of claim 3.

15. An ophthalmic device comprising the ophthalmic device material of claim 4.

16. The ophthalmic device of claim 15 wherein the ophthalmic device is selected from the group consisting of an intraocular lens; a contact lens; a keratoprosthesis; and a corneal inlay or ring.

* * * * *